United States Patent
Minar et al.

(10) Patent No.: US 7,627,382 B2
(45) Date of Patent: Dec. 1, 2009

(54) MEDICAL DEVICES WITH AROMATIC POLYIMIDE COATING

(75) Inventors: Chris Minar, New Prague, MN (US); Andrew Senn, Chanhassen, MN (US); William Whealon, Chaska, MN (US); Bruce Rittenour, Princeton, MN (US)

(73) Assignee: Lake Region Manufacturing, Inc., Chaska, MN (US)

( * ) Notice: Subject to any disclaimer, the term of this patent is extended or adjusted under 35 U.S.C. 154(b) by 601 days.

(21) Appl. No.: 11/137,162

(22) Filed: May 25, 2005

(65) Prior Publication Data

US 2006/0271135 A1 Nov. 30, 2006

(51) Int. Cl.
*A61N 1/04* (2006.01)

(52) U.S. Cl. ..................................... 607/115

(58) Field of Classification Search ................ 607/115; 528/351

See application file for complete search history.

(56) References Cited

U.S. PATENT DOCUMENTS

| | | | |
|---|---|---|---|
| 3,168,417 A * | 2/1965 | Smith, Jr et al. ............ | 428/383 |
| 3,179,614 A | 4/1965 | Edwards | |
| 3,179,630 A | 4/1965 | Endrey | |
| 3,179,631 A | 4/1965 | Endrey | |
| 3,179,632 A | 4/1965 | Hendrix | |
| 3,179,633 A | 4/1965 | Endrey | |
| 3,179,634 A | 4/1965 | Edwards | |
| 3,287,311 A | 11/1966 | Edwards | |
| 3,990,098 A | 11/1976 | Mastrangelo | |
| 4,056,651 A | 11/1977 | Scola | |
| 4,505,767 A | 3/1985 | Quin | |
| 4,925,445 A | 5/1990 | Sakamoto et al. | |
| 4,939,317 A | 7/1990 | Hostler | |
| 5,069,226 A | 12/1991 | Yamauchi et al. | |
| 5,147,966 A | 9/1992 | St. Clair et al. | |
| 5,171,828 A | 12/1992 | Meterko et al. | |
| 5,184,627 A | 2/1993 | de Toledo | |
| 5,210,174 A | 5/1993 | Tamai et al. | |
| 5,433,200 A | 7/1995 | Fleischhacker | |
| 5,464,928 A | 11/1995 | Chang et al. | |
| 5,478,916 A | 12/1995 | Chang et al. | |
| 5,502,157 A | 3/1996 | Chang et al. | |
| 5,639,850 A | 6/1997 | Bryant | |
| 5,669,383 A * | 9/1997 | Johnson ...................... | 600/434 |
| 5,741,883 A | 4/1998 | Bryant | |
| 5,760,341 A | 6/1998 | Laske et al. | |
| 6,048,959 A | 4/2000 | Bryant | |
| 6,379,369 B1 | 4/2002 | Abrams et al. | |
| 6,919,422 B2 * | 7/2005 | Gallucci et al. ............. | 528/353 |
| 6,997,947 B2 | 2/2006 | Walak | |
| 2003/0216800 A1 | 11/2003 | Ebert et al. | |
| 2005/0004643 A1 | 1/2005 | Ebert et al. | |

FOREIGN PATENT DOCUMENTS

| | | |
|---|---|---|
| EP | 1192957 A2 | 4/2002 |
| JP | 2159247 | 6/1990 |
| WO | 8804940 | 7/1988 |

OTHER PUBLICATIONS

Varner, S.J., "Characterization of polyimides by C and H solid state nuclear magnetic resonance", Solid State Nuclear Magnetic Resonance, vol. 12, Issues 2-3, Sep. 1998, pp. 71-85.

Miner, Gilda A., et al, "The Wettability of LaRC Colorless Polyimide Resins on Casting Surfaces", 1997 American Chemical Society National Meeting, San Francisco, CA, Apr. 13-17, 1997.

Schmidt, John A., et al, "Bipolar Pacemaker Leads: New Materials, New Technology", Journal of Investigative Surgery, vol. 11, 1998, pp. 75-81.

* cited by examiner

*Primary Examiner*—Carl H Layno
*Assistant Examiner*—Brian T Gedeon
(74) *Attorney, Agent, or Firm*—Whyte Hirschboeck Dudek S.C.

(57) ABSTRACT

Medical devices that include on at least some portion thereof an aromatic polyimide of the structure:

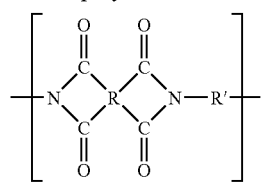

(I)

wherein R is a tetravalent aromatic radical, preferably containing at least one ring of six carbon atoms, said ring characterized by benzenoid unsaturation, the four carbonyl groups being attached directly to separate carbon atoms in a ring and each pair of carbonyl groups being attached to adjacent carbon atoms in a ring of the R radical; and wherein R' is a divalent benzenoid radical selected from the group consisting of

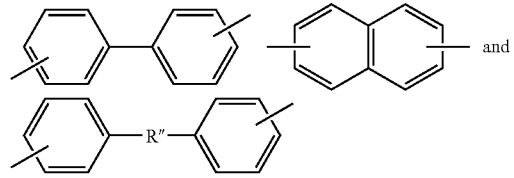

wherein R" is selected from the group consisting of an alkylene chain having 1-3 carbon atoms,

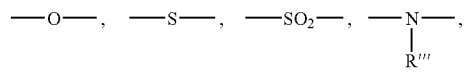

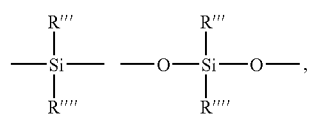

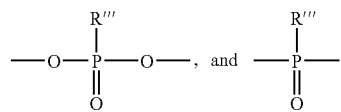

R'" and R"" are selected from the group consisting of alkyl and aryl.

In one embodiment the medical device is a coated lead body.

Coated guide wires are a further embodiment.

Methods of application are a further embodiment.

37 Claims, 5 Drawing Sheets

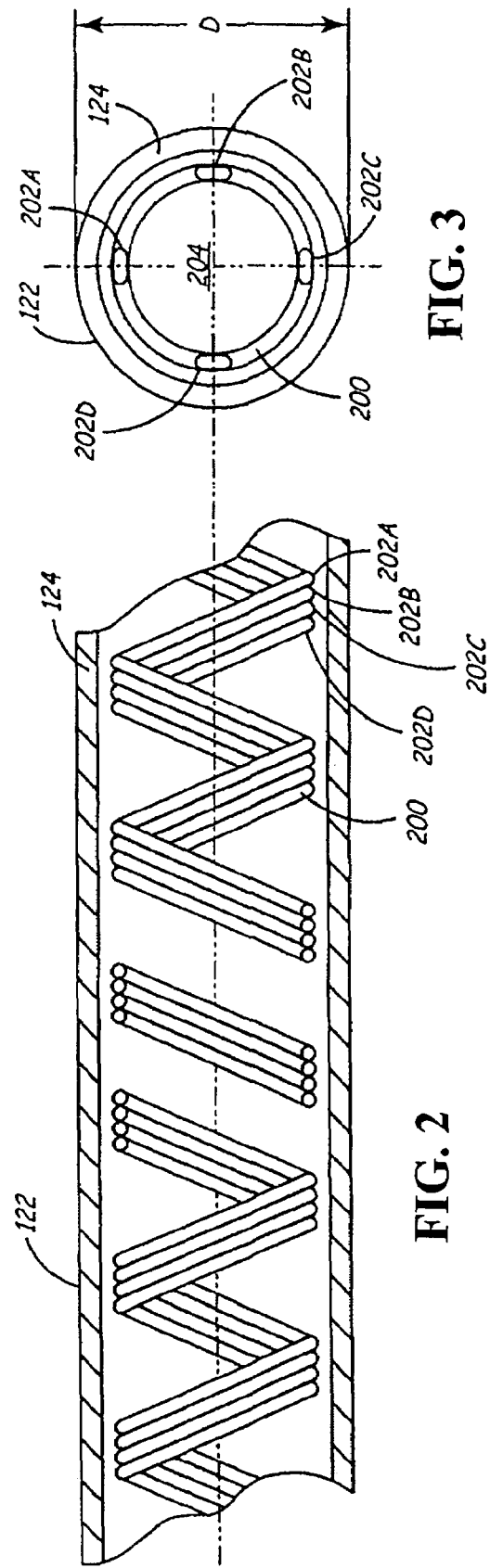

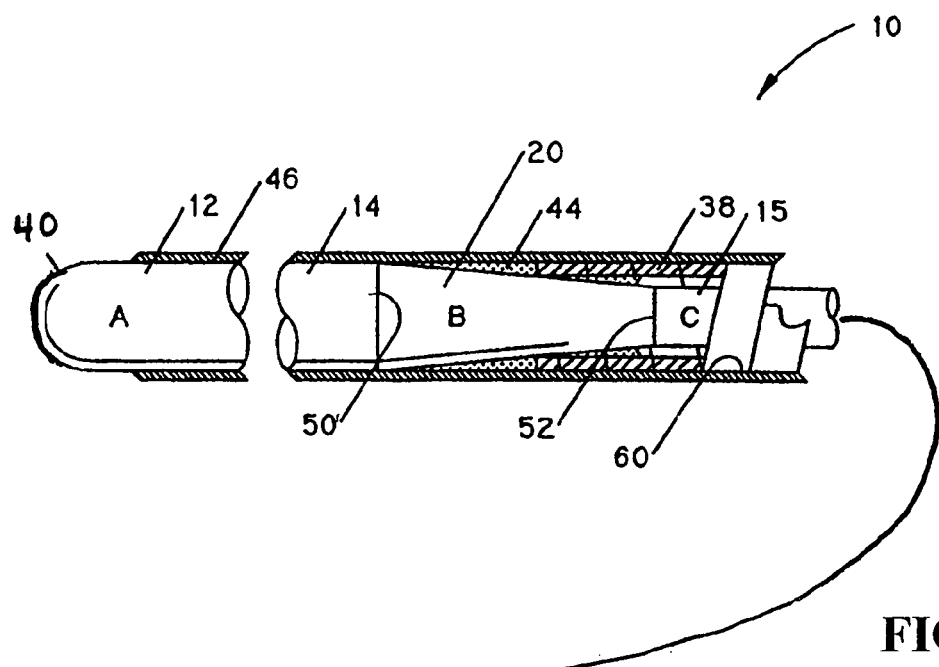
FIG. 7
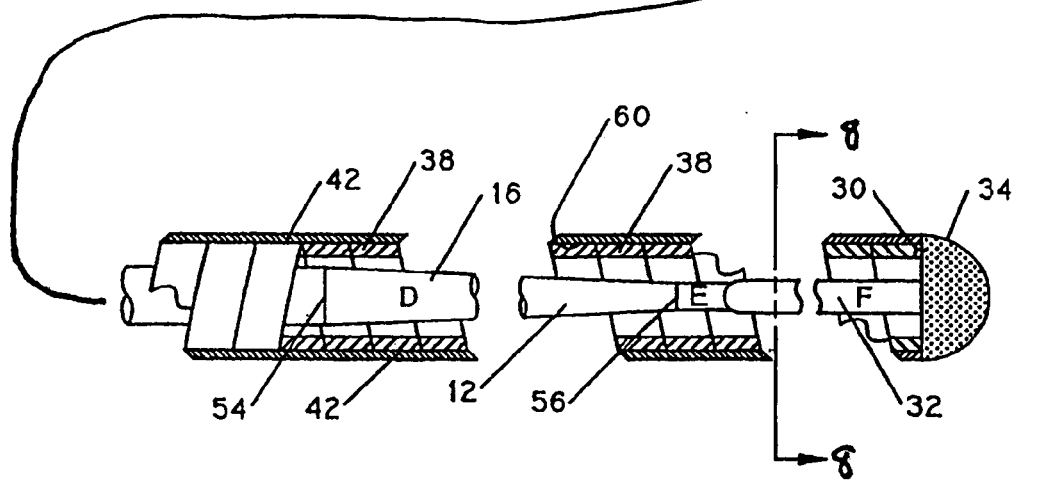
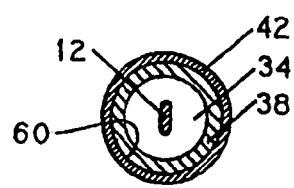
FIG. 8

MEDICAL DEVICES WITH AROMATIC POLYIMIDE COATING

CROSS-REFERENCE TO RELATED APPLICATIONS

Not Applicable.

FIELD OF THE INVENTION

Medical devices generally have either acute or chronic applications. This invention relates generally to medical devices for either or both of acute or chronic applications which have novel aromatic polyimide coatings thereon. The present invention relates in part, to implantable medical device leads for delivering therapy, in the form of electrical stimulation. In particular, the present invention relates to conductor coil insulation in implantable medical device leads.

BACKGROUND OF THE INVENTION

Chronically implantable medical electrical leads are well known in the fields of cardiac stimulation and monitoring, including neurological stimulation and cardiac pacing and cardioversion/defibrillation. In the field of cardiac stimulation and monitoring, so called endocardial leads are placed through a transvenous route to position one or more sensing and/or stimulation electrodes in a desired location within a heart chamber or interconnecting vasculature. During this type of procedure, a lead is passed through the subclavian, jugular, or cephalic vein, into the superior vena cava, and finally into a chamber of the heart or the associated vascular system. An active or passive fixation mechanism at the distal end of the endocardial lead may be deployed to maintain the distal end of the lead at a desired location.

It is highly desirable that implantable leads have the lowest possible profile while the insulation maintain sufficient integrity to electrically isolate one or more conductors of the leads over the life of the implanted lead.

Medical guide wires are used in many medical procedures. Guide wires, which are generally pushable, rotatable (torquable) and steerable, are used primarily to help position other medical devices, e.g., catheters, within a patients' vasculature. Advantageously coated guide wires are a long term interest of the medical world.

SUMMARY OF THE INVENTION

Briefly, in one aspect, the present invention is a medical device, whether for chronic or acute applications, having a chemically stable, dielectrically advantageous, aromatic polyimide coating thereon. Medical devices upon which the aromatic polyimide of this invention may be coated include without limitations, chronically implanted devices such as electrical stimulation, leads (PCD's, neurological stimulation devices for mitigation of pain, drug pumps, insulin pumps, and cochlear stimulation devices) as well as acutely used devices such as guide wires.

"Aromatic polyimide" as the term is used herein means polyimides characterized by a recurring unit having the following structural formula:

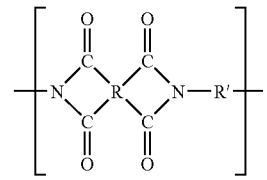

wherein R is a tetravalent aromatic radical, preferably containing at least one ring of six carbon atoms, said ring characterized by benzenoid or aromatic unsaturation, the four carbonyl groups being attached directly to separate carbon atoms in a ring and each pair of carbonyl groups being attached to adjacent carbon atoms in a ring of the R radical; and wherein R' is a divalent benzenoid radical selected from the group consisting of

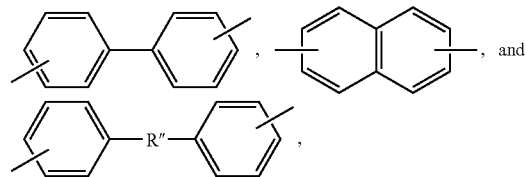

wherein R" is selected from the group consisting of an alkylene chain having 1-3 carbon atoms,

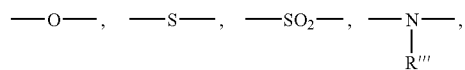

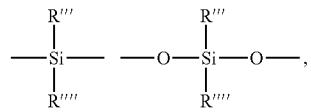

wherein R''' and R'''' are selected from the group consisting of alkyl and aryl.

A particularly preferred aromatic polyimide, especially for coatings on electrically conductive, chronically implanted pacing leads, is one in which

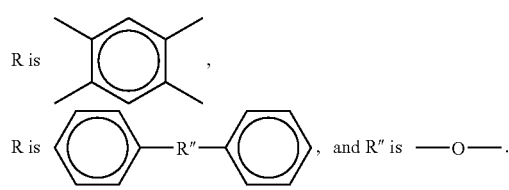

Thus the particularly preferred aromatic polyimide has the recurring unit

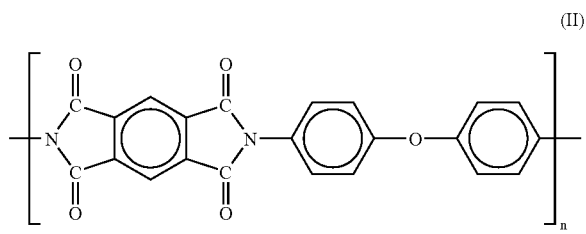

(II)

Generally speaking n has a value in the range of about 50 to 500, preferably about 60 to 400, and most preferably about 100 to about 350. One skilled in the art will appreciate that for some applications the value of n is not particularly important, the chemical characteristics being dictated by the recurring unit rather than molecular weight ("n").

The polyimides of the present invention display outstanding physical and chemical properties which make them very useful when applied to medical devices according to this invention. Aromatic polyimide coatings of the invention are characterized by high tensile properties, desirable electrical properties, and surprising stability to heat and water. They are particularly resistant to body fluids.

BRIEF DESCRIPTION OF THE DRAWINGS

The following drawings are illustrative of particular embodiments of the invention and therefore do not limit its scope, but are presented to assist in providing a proper understanding of the invention. The drawings are not to scale (unless so stated) and are intended for use in conjunction with the explanations in the following detailed description. Embodiments of the present invention will hereinafter be described in conjunction with the appended drawings, wherein like numerals denote like elements, and:

FIG. 2 is a cross-sectional view of a lead of the exemplary device taken along cross-sectional lines III-II of FIG. 1;

FIG. 3 is a cross-sectional view of the lead of the exemplary device taken along cross-sectional lines II-III of FIG. 1;

FIG. 7 shows in schematic form, in partial section, a guidewire on which a coating of the present invention could be utilized.

FIG. 8 is a cross-sectional view of the guidewire of FIG. 7 taken along line 8-8 of FIG. 7.

DETAILED DESCRIPTION OF THE INVENTION

Figure 1:
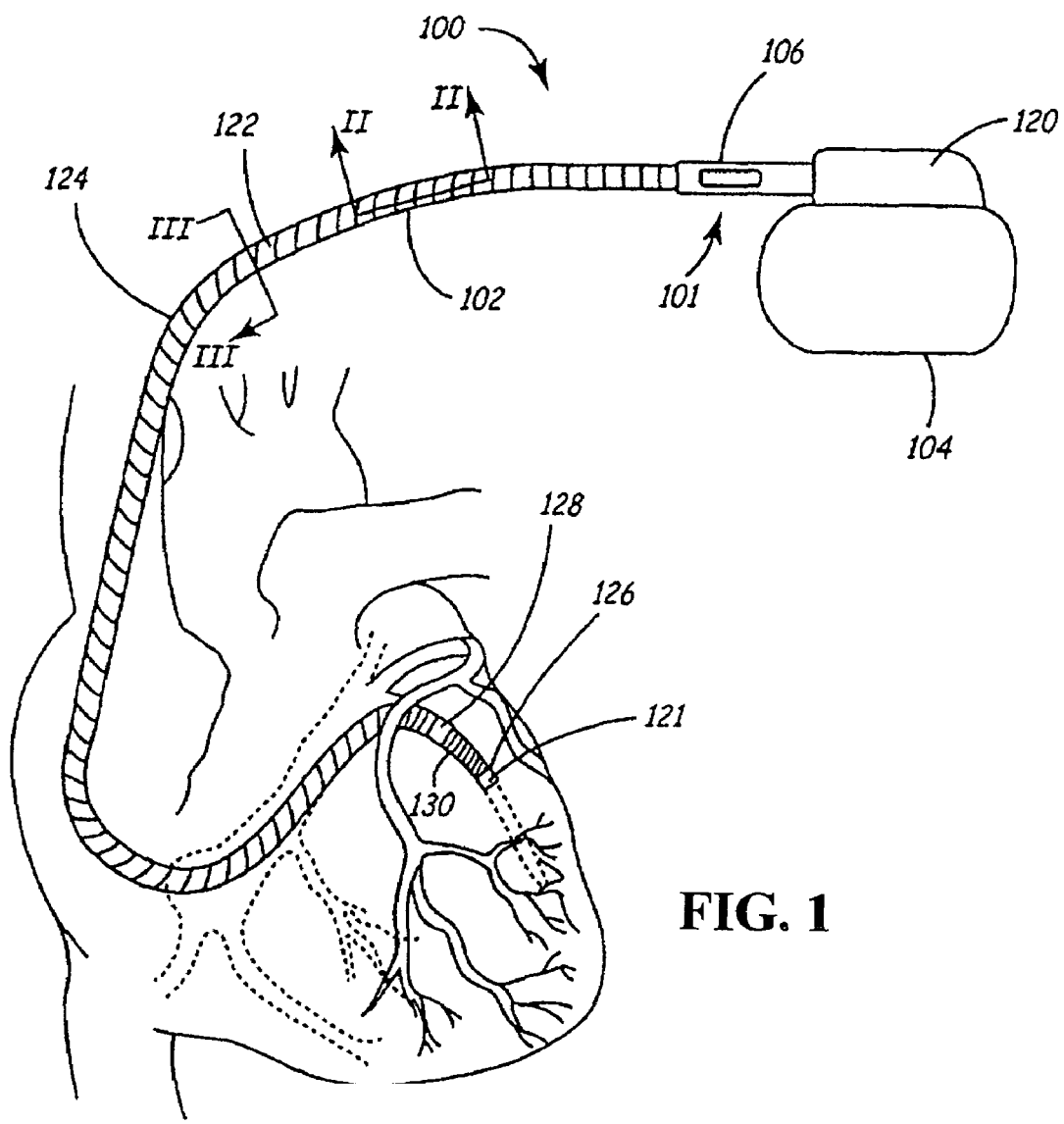
FIG. 1 is a schematic diagram of an exemplary implantable medical device in accordance with one embodiment of the present invention.

FIG. 1 is a schematic diagram of an exemplary implantable medical device in accordance with one embodiment of the present invention. As illustrated in FIG. 1, an implantable medical device 100 according to the present invention includes an implantable medical device lead 102 and an implantable medical device housing 104, such as an implantable cardioverter/defibrillator or pacemaker/cardioverter/defibrillator (PCD). The PCD, for example, processes cardiac data sensed through lead 102 and generates electrical signals in response to the sensed cardiac data for the provision of cardiac pacing, cardioversion and defibrillation therapies. A connector assembly 106 located at a proximal end 101 of lead 102 is insertable within a connector block 120 of housing 104 to electrically couple lead 102 with electronic circuitry (not shown) of housing 104.

Lead 102 includes an elongated lead body 122 that extends between proximal end 101 and a distal end 121 of lead 102. An outer insulative sheath 124 surrounds lead body 122 and is preferably fabricated of polyurethane, silicone rubber, a fluoropolymer or a combination thereof. Coiled wire conductors, in accordance with one embodiment of the present invention, are positioned within lead body 122, as will be described in detail below. Distal end 121 of lead 102 includes, in this embodiment, a proximal ring electrode 128 and a distal tip electrode 126, separated by an insulative sleeve 130. Proximal ring electrode 128 and distal tip electrode 126 are electrically coupled to connector assembly 106 by one or more coil conductors, or filars extending between distal end 121 and proximal end 101 of lead 102 in a manner well known to one skilled in the electro-therapy art. Many other combinations of implantable medical device housings, connector assemblies and lead configurations will occur to one skilled in this art. All such combinations are within the contemplation of this invention.

FIG. 2 is a cross-sectional view of a lead of the exemplary device taken along cross-sectional lines II-II of FIG. 1. As illustrated in FIG. 2, lead 102 of implantable medical device 100 includes a quadrafilar conductor coil 200 including four individual filars, or coiled wire conductors 202A, 202B, 202C and 202 extending within insulative sheath 124 of lead body 122. Coiled wire conductors 202A-202D electrically couple proximal ring electrode 128 and distal tip electrode 126 with connector assembly 106. It is understood that although the present invention is described throughout in the context of a quadrafilar conductor coil, having each of two electrodes electrically coupled to a connector assembly via two of the four individual coiled wire conductors, the present invention is not intended to be limited to application in a quadrafilar conductor coil. Rather, the lead conductor insulator of the present invention can be utilized in any conductor configuration, including the use of any number of conductor coils depending upon the number of desired electrodes, and would include the use of a single filar electrically coupling the electrode to the connector.

FIG. 3 is a cross-sectional view of the lead of the exemplary device taken along cross-sectional lines III-III of FIG. 1. As illustrated in FIGS. 2 and 3, each of the individual filars or coiled wire conductors 202A, 202B, 202C and 202D are parallel-wound in an interlaced manner to have a common outer and inner coil diameter. As a result, conductor coil 200 forms an internal lumen 204, which allows for passage of a stylet or guide wire within lead 102 to direct insertion of lead 102 within the patient.

Alternately, lumen 204 may house an insulative fiber, such as ultrahigh molecular weight polyethylene (UHMWPE), liquid crystal polymer (LCP), polyester and so forth, or an insulated cable (i.e. cable 630 illustrated in FIG. 6) in order to allow incorporation of an additional conductive circuit and/or structural member to aid in chronic removal of lead 102 using traction forces. Such an alternate embodiment would require insertion and delivery of lead 102 to a final implant location using alternate means, such as a catheter, for example. Lumen 204 may also include an insulative liner (not shown), such as a fluoropolymer, polyimide, PEEK, for example, to prevent damage caused from insertion of a style/guidewire (not shown) through lumen 204.

Figure 4:
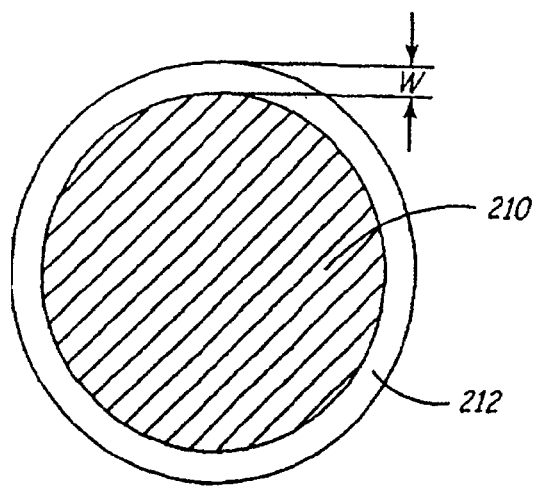
FIG. 4 is a cross-sectional view of a coiled wire conductor forming a filar of a multi-filar conductor coil according to one embodiment of the present invention.

FIG. 4 is a cross-sectional view of a coiled wire conductor forming a multi-filar conductor coil according to some embodiments of the present invention. As illustrated in FIG. 4, one or more of the individual coiled wire conductors 202A, 202B, 202C and 202D includes a conductor wire 210 surrounded by an insulative layer 212. According to one aspect of the present invention, insulative layer 212 is formed of an aromatic polyimide as is described in greater detail below. The thickness of the insulative layer 212 ranges from approximately 0.0001 inches up to approximately 0.0050 inches, forming a corresponding wall thickness W of the insulative layer 212. By utilizing the aromatic polyimide as an insulative layer 212, the present invention provides an improved electrically insulating material that is stable for chronic e.g., implantable applications (in vivo) and in acute applications e.g., guide wires, stylettes, etc.

Figure 5:
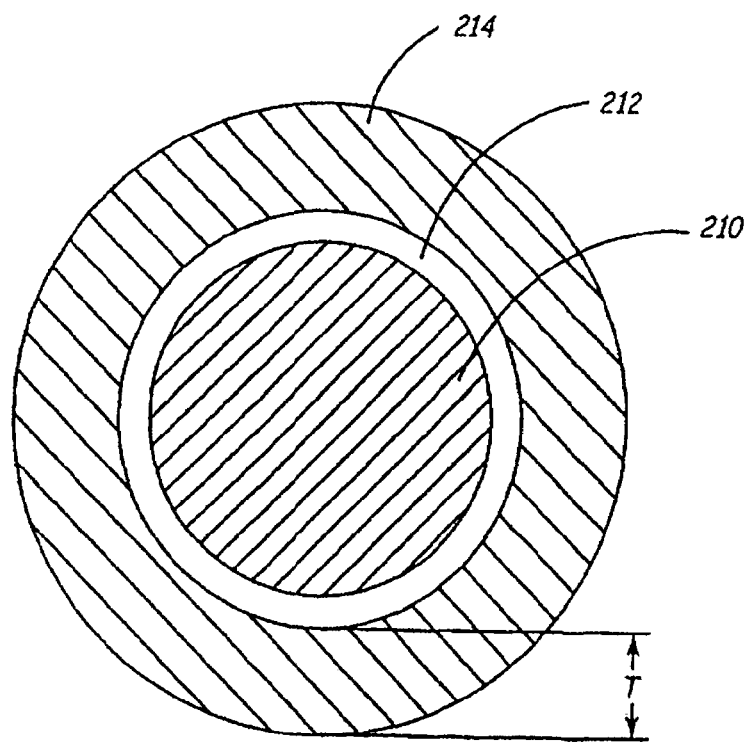
FIG. 5 is a cross-sectional view of a coiled wire conductor forming a filar of a multi-filar conductor coil according to another embodiment of the present invention.

FIG. 5 is a cross-sectional view of a coiled wire conductor forming a multi-filar conductor coil according to another embodiment of the present invention. The insulative layer 212 of aromatic polyimide according to the present invention can be utilized as a stand-alone insulation on a filar or as an initial layer of insulation followed by an additional outer layer or sleeve as redundant insulation to enhance reliability. For example, according to an embodiment of the present invention illustrated in FIG. 5, in addition to conductor wire 210 and insulative layer 212, one or more of the individual coiled wire conductors 202A, 202B, 202C and 202D includes an additional outer insulative layer 214, formed of known insulative materials, such as ETFE, for example, to enhance reliability of the lead. According to the present invention, insulative layer 214 generally has a thickness T between approximately 0.0005 and 0.0025 inches, for example, although other thickness ranges are contemplated by the present invention. Since the outermost insulative layer, i.e., insulative layer 214, experiences more displacement during flex of lead 102 than insulative layer 212, it is desirable for insulative layer 214 to be formed of a lower flex modulus material than insulative layer 212, such as ETFE.

By utilizing the insulative layer 212 of the present invention, the stimulating lead is reduced in diameter, and is more robust in regards to mechanical flex and electrical insulation. The insulative layer 212 provides an extremely long-term flex-life performance associated with the ductility of the aromatic polyimide coating over conductor wires such as MP35N, used on conductor coils. These improved properties are related to the unique process of the multiple pass application of the aromatic polyimide and to the properties for the aromatic polyimide itself. The resulting insulative layer 212 provides a highly reliable insulating and mechanically robust coating over implantable stimulation leads and to the properties of the polyimide itself. We may want to add something related to line [0068] related to the unique dielectric properties compared to published values.

While an insulative layer formed only of ETFE tends to be susceptible to creep, insulative layer 212 of the present invention, which is formed of aromatic polyimide, is mechanically more robust, dimensionally stable and possesses exceptionally dielectric properties, making the aromatic polyimide desirable for long-term implant applications. The use of a thin layer of aromatic polyimide coating on e.g., conventional MP35N alloy coil filars, may also act as a protective barrier to reduce the incidence of metal induced oxidation seen on some polyurethane medical device insulations According to one embodiment of the present invention, the insulative layer 212 is applied onto the conductor wire 210 in multiple coats, that is, layer 212 is comprised of multiple layers of an aromatic polyimide resulting in a desired wall thickness W. The coating is applied in such a way to provide a ductile, robust insulative layer that enables a single filar, i.e., coiled wire conductor, or multiple filar, i.e., coiled wire conductors, to be wound into a single wound conductor coil 200 of sizes ranging from an outer diameter D (FIG. 3) of 0.010 inches to 0.110 inches. For example, the coating process includes an oven cure cycle to drive off the solvents and create the polyimide. Column 7, line 63 to Column 8, line 14 of U.S. Pat. No. 4,056,651, which is incorporated herein by reference, describes a coating procedure which may be employed to manufacture embodiments of the present invention. According to an exemplary embodiment, wire 210, having a diameter between approximately 0.003 inch and approximately 0.005 inch, after being cleaned with an alkaline solution, undergoes up to 30 multiple coating cycles through self-centered dies resulting in wall thickness W of approximately 0.0005 inch. Each coating cycle is followed by a high temperature curing cycle. To assure an adequate toughness and flexibility of each imidized coating layer, that is to prevent cracking upon subsequent processing of the coated wire, each layer should be exposed to a high enough temperature, for example an oven temperature between approximately 650 degrees F. and approximately 850 degrees F., for a sufficient time to drive off residual solvent. Thus, multiple coating passes forming insulative layer 212 on conductor wire 210 provide the ductility that is needed to make the coated conductor wire 210 into a conductor coil 200 that can withstand the long term flex requirements of an implantable lead. However, according to an alternate embodiment, one or more wire filars may be wound into a coiled configuration prior to applying a layer or layers of an aromatic polyimide. Spraying and extrusion processes known to those skilled in the art may also be employed to manufacture embodiments of the present invention.

The use of an aromatic polyimide insulative layer 212 according to the present invention offers an exceptional dielectric strength for electrical insulation. Through flex studies on conductor coils coated with the aromatic polyimide, it has been found that the insulative layer 212 also has high flex properties in regards to stimulating lead conductor coil flex testing. The aromatic polyimide coating in various wall thicknesses will remain intact on the coil filar until the coil filar fractures as seen in conventional conductor coil flex studies (reference 10 million to 400 million flex cycles at various 90 degree radius bends).

Conductor coils 200 (FIG. 2) according to the present invention can include a single filar or multiple filars, with each filar being an individual circuit that could be associated with a tip electrode, a ring electrode, a sensor, and so forth. The dielectric properties of aromatic polyimide coating of this invention when coated on e.g., individual lead filars, enable the use of multiple circuits in a single conductor coil, resulting in a downsizing of the medical device on which the polyimides are used. For example, there is approximately a 40 to 50 percent reduction in lead size between known bipolar designs, which traditionally utilized an inner coil and inner insulation, outer coil and outer insulation, to a lead design having multiple circuits in a single conductor coil having an aromatic polyimide insulative layer 212 according to the present invention.

Aromatic polyimides as described herein do not show a notable decrease in mechanical performance over time when immersed in an aqueous environment, such as an implant environment.

Figure 6:
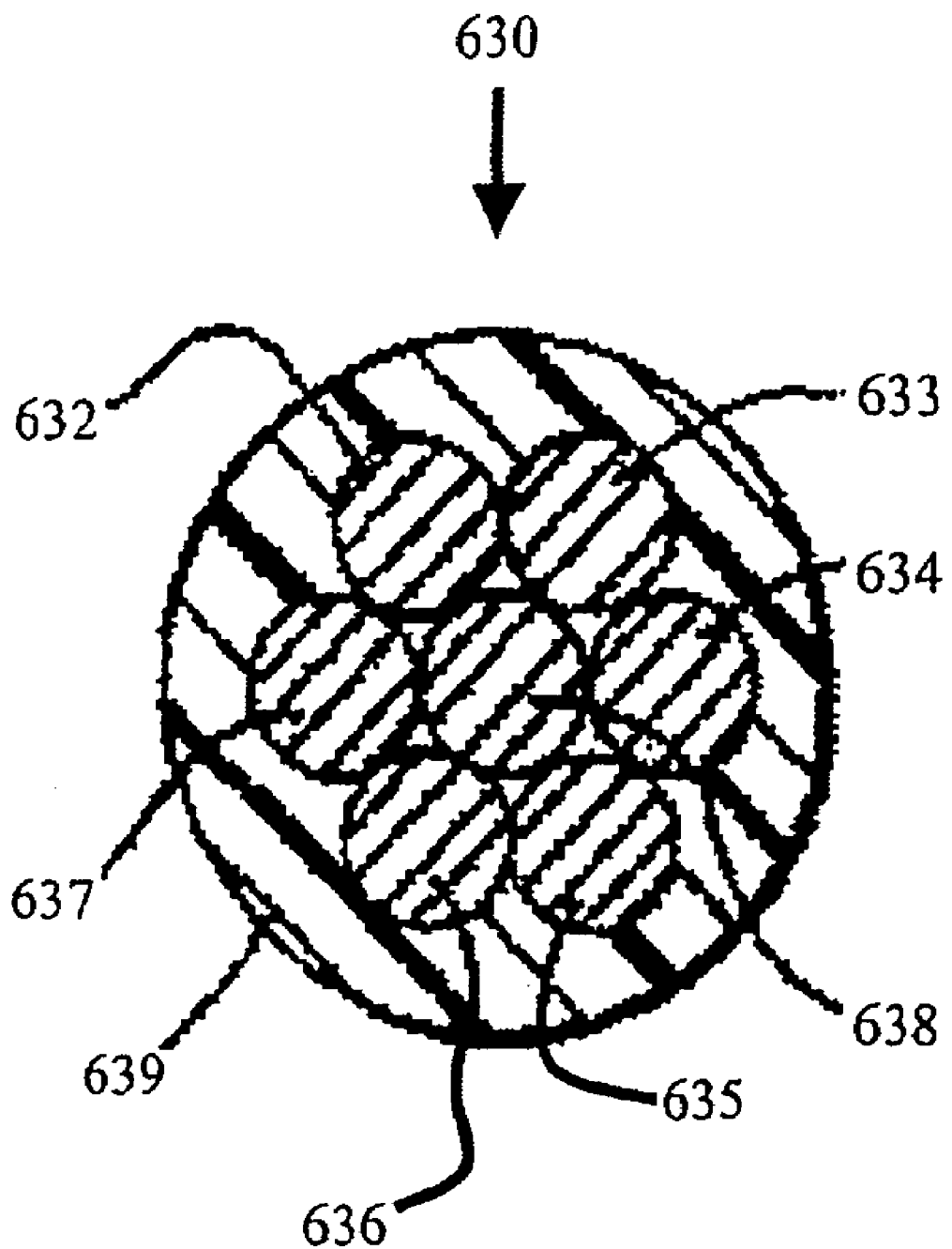
FIG. 6 is a cross-sectional view of an exemplary cabled wire conductor according to yet another embodiment of the present invention.

FIG. 6 is a radial cross-section of an exemplary cabled wire conductor according to yet another embodiment of the present invention. FIG. 6 illustrates cable 630 including bundled wire strands 632-637 formed about a core wire strand 638, any or all of which strands may be formed from a Co—Ni—Cr—Mo alloy, MP35N, or any other conductive corrosion-resistant and biocompatible material of sufficient strength and toughness for incorporation into a medical electrical lead; a diameter of each wire strand in various embodiments is between approximately 0.0005 inch and 0.005 inch. Using a conventional stranding machine, wire strands 632-638 are each tightly bundled in a cable-like fashion; a lay or pitch of stranding is typically between 0.3 inch and 0.6 inch. As is further illustrated in FIG. 6, cable 630 includes an insulating layer 639 surrounding bundled wire strands 632-638, which is formed from an aromatic polyimide, examples of which have been previously described. It should be noted that, although FIG. 6 illustrates insulating layer 639 surrounding the plurality of wire strands as bundled, according to an alternate embodiment, one or more of each of the individual wire strands include an insulating layer of an aromatic polyimide, for example as illustrated in FIG. 4, and layer 639 may or may not be included. Another type of cable configuration, which may include an aromatic polyimide insulating layer, is described in U.S. Pat. No. 5,760,341, issued to Laske et al., the teachings of which are incorporated by reference herein.

According to one embodiment, layer 639 may be applied to the bundled wire strands 632-638 by passing them through a polyamide acid solution and then heating the strands to a temperature sufficient to fully imidize the polyimide. Layer 212 may be applied to conductor 210 in a similar manner. As previously described, multiple coating passes may form layers 630 and 212. According to an alternate embodiment an extrusion process may be used to apply layer 639 or layer 212. According to yet another embodiment a second layer of another, insulative material is formed over layer 639, for example a layer of ETFE, as described in conjunction with FIG. 5.

FIG. 7 illustrates one example of a guidewire utilizing the coating of the present invention. This guidewire is the subject of U.S. Pat. No. 5,433,200 issued Jul. 18, 1995, which is incorporated herein by reference in its entirety. Specifically, FIG. 7 is a plan view of a guidewire 10, of at least a portion of guidewire 10 having a coating 42 thereon. The specific details of construction of the guidewire are not critical to the present invention. As is shown, coating 42 extends from approximately the proximal end of guidewire 10 (designated on the wire core at "A") essentially all the way to the atraumatic distal tip 34 (segment "F"). One skilled in the art will appreciate that less than the entire exterior surface of a guidewire may be coated with an aromatic polyimide of the present invention. The remaining details of the guidewire shown in FIG. 7 are disclosed at column 3, line 55 through column 5, line 27 of the afore-mentioned U.S. Pat. No. 5,433,2000 patent that, disclosure being specifically incorporated by reference herein.

FIG. 8 is a cross sectional view of the guidewire shown in FIG. 7 taken along line 7-7 thereof. Coating 42 is specifically shown in FIG. 8.

The aromatic polyimides used as coatings in this invention may be prepared by reacting at least one organic diamine having the structural formula

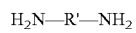

wherein R' is a divalent benzenoid radical selected from the group consisting of

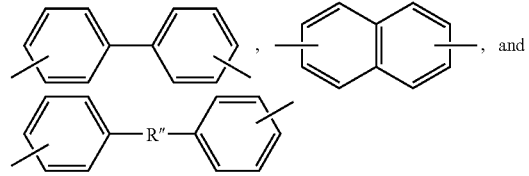

wherein R" is selected from the group consisting of an alkylene chain having 1-3 carbon atoms,

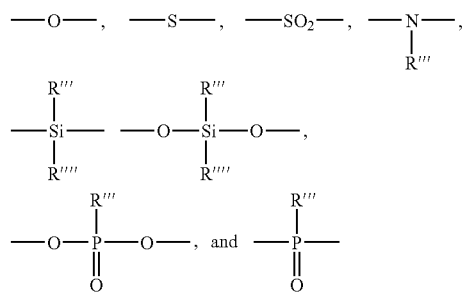

wherein R''' and R'''' are selected from the group consisting of alkyl and aryl, with at least one tetracarbozylic acid dianhydride having the structural formula:

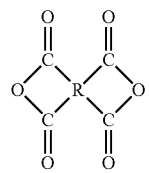

wherein R is a tetravalent aromatic organic radical, preferably containing at least one ring of six carbon atoms, said ring characterized by benzenoid unsaturation, the four carbonyl groups being attached directly to separate carbon atoms in a ring and carbon atoms of each pair of carbonyl groups being attached to adjacent carbon atoms in a ring of the radical.

A preferred aromatic polyimide for use in the present invention is sold under the trade designation PRYE™ ML and is commercially available from Industrial Summit Technology of Parlin, N.J., U.S.A. A particularly preferred material is one in which R is tetravalent benzene i.e.,

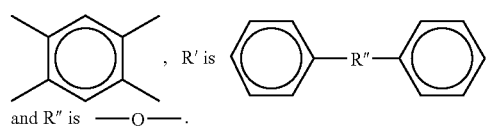

and R" is —O—.

Putting these moieties together provides a repeating unit shown at Formula II, above.

The preferred material is an aromatic polyimide resulting from conversion of a polyamide which is itself the condensation product of

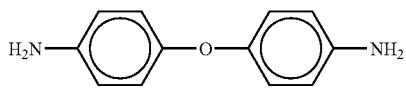

4,4' diaminodiphenyl ether and

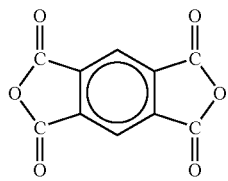

Pyromellitic dianhydride.

The diamine and the dianhydride may be reacted directly. Alternatively, the dianhydride may first be reacted with a mono-functional alcohol (ethanol) to form a monomeric diester-diacid which is then reacted with the diamine. As a third alternative, any combination of the foregoing two techniques may be used. In all of these techniques melt polymerization is performed under such conditions to form the polyimide directly.

However, the preferred process involves first preparing a polyamide-acid having an inherent viscosity of at least 0.1, preferably 0.3-5, by the reaction of the diamine and the dianhydride in an organic solvent for at least one of the reactants, the solvent being inert to the reactants, preferably under substantially anhydrous conditions for a time and at a temperature below 175° C., sufficient to provide in most instances at least 50% of the corresponding polyamide-acid, and then converting the polyamine-acid to the polyimide, the polyimide also having an inherent viscosity of at least 0.1, preferably 0.3-5.

The inherent viscosity of the polyimide is measured at 30° C. as a 0.5% solution in a suitable solvent for the polyimide. For many polyimides of this invention, concentrated (96%) sulfuric acid is a suitable solvent. However, the solvent may be selected from a group consisting of concentrated sulfuric acid, fuming nitric acid, the monohydrate of sym-dichlorotetrafluoroacetone and the hydrate of onochloropentafluoroacetone. It has been found that if the polyimide is not soluble in concentrated sulfuric acid to the extent of 0.5%, then its inherent viscosity in a suitable solvent can usually be considered to be greater than 0.1. For example, poly bis (4 aminophenyl) ether pyromellitimide prepared by this invention may not be soluble to the extent of 0.5% in concentrated sulfuric acid, yet it displays an inherent viscosity greater than 0.1 when measured as a 0.5% solution in the monohydrate of sym-dichloroetetrafluoroacetone or in fuming nitric acid.

It should also be understood that the polymers may be modified with inert materials prior to or after application. These modifying agents may be selected from a variety of types such as pigments, dyes, inorganic and organic fillers, radiopacity-providing agents, etc.

Furthermore, in determining a specific time and a specific temperature for forming the polyamide-acid of a specified diamine and a specified dianhydride, several factors must be considered. Generally the maximum permissible temperature will depend on the diamine used, the dianhydride used, the particular solvent, the percentage of polyamide-acid desired in the final composition and the minimum period of time that one desires for the reaction. For most combinations of diamines and dianhydrides falling within the definitions given above, it is possible to form compositions of 100% polyamide-acid by conducting the reaction below 100° C.

The particular temperature below 175° C. that must not be exceeded for any particular combination of diamine, dianhydride, solvent and reaction time will vary but can be determined by a simple test by any person of ordinary skill in the art. However, to obtain the maximum inherent viscosity, i.e., maximum degree of polymerization, for any particular combination of diamine, dianhydride, solvent, etc., it has been found that the temperature throughout the reaction generally should be maintained below 60° C., preferably below 50° C.

The details of a preferred process involve premixing equimolar amounts of the diamine and the dianhydride as dry solids and then adding the mixture, in small proportions and with agitation, to the organic solvent. Premixing the ingredients and then adding them in small proportions to the solvent provides relatively simple means for controlling the temperature and the rate of the process. Since the reaction is exothermic and tends to accelerate very rapidly, it is important to regulate the additions to maintain the reaction temperature at the desired level. However, the order of addition may be varied. After premixing the diamine and the dianhydride, the solvent may be added to the mixture with agitation. It is also possible to dissolve the diamine in the solvent while agitating, preheating the solution and then adding the dianhydride at a sufficiently slow rate to control of the polymer in a suitable solvent, e.g., N,N-dimethylacetamide.

To calculate inherent viscosity, the viscosity of the polymer solution is measured relative to that of the solvent alone.

$$\text{Inherent viscosity} = \frac{\text{natural logarithim} \frac{\text{Viscosity of solution}}{\text{Viscosity of solvent}}}{C}$$

Where C is the concentration expressed in grams of polymer per 100 milliliters of solution. As is known in the polymer art, inherent viscosity is directly related to the molecular weight of the polymer.

The quantity of organic solvent used in the preferred process need only be sufficient to dissolve enough of one reactant, preferably the diamine, to initiate the reaction of the diamine and the dianhydride. The viscous solution of the polymeric composition containing at least 50% polyamide-acid in the polymeric component dissolved in the solvent is preferred.

It should be understood that the conversion processes to be described also apply to compositions containing the reaction temperature. Ordinarily, in this latter process the last portion of the dianhydride is added with part of the organic solvent. Another possible method involves adding the reactants to the solvent in small proportions, not as a pre-mixture and alternately; first diamine, then dianhydride, then diamine, etc. In any event, it is advisable to agitate the solution polymerization system after the additions are completed until maximum viscosity denoting maximum polymerization is obtained. Still another process involves dissolving the diamine in one portion of a solvent and the dianhydride in another portion of the same or another solvent and then mixing the two solutions.

The degree of polymerization of the polyamide-acid is subject to deliberate control. The use of equal molar amounts of the reactants under the prescribed conditions provides polyamide-acids of very high molecular weight. The use of either reactant in large excess limits the extent of polymerization. Besides using an excess of one reactant to limit the molecular weight of the polyamide-acid, a chan terminating agent e.g., phthalic anhydride optionally may be used to "cap" the ends of the polymer chains.

In the preparation of the polyamide-acid intermediate, it is essential that the molecular weight be such that the inherent viscosity of the polymer is at least 0.1, preferably 0.3-5.0. The inherent viscosity of the polyamide-acid is measured at 30° C.

at a concentration of 0.5% by weight at least 50% of the salt derivatives of polyamide-acids, e.g., the triethyl ammonium salt of the polyamide-acids, instead of the polyamide-acids themselves.

As was noted above, the polyamide-acid composition in the solvent may be used as a liquid coating composition. Such coating compositions may be pigmented with such compounds as titanium dioxide in amounts of 5-200% by weight. These coating compositions may be applied to a variety of substrates, for example, metals, e.g., copper, brass, aluminum, steel, etc., the metals in the form of sheets, fibers, foams, fabrics, etc.; polymeric materials used as part of a medical device, e.g., cellulosic materials such as cellophane, wood, paper, etc., polyofins such as polyethylene, polypropylene, polystyrene, etc., polyesters such as polyethylene terephthalate, etc., perfluorocarbon polymers such as polytetrafluoroethylene, copolymers of tetrafluoroethylene with hexafluoropropylene, etc., polyurethanes, all polymeric materials in the form of sheets, fibers, foams, woven and non-woven fabrics, screening, etc.; leather sheets; etc. The preferred application is for medical device components (or entire devices) which require the dielectric properties shown by these aromatic polyimides as well as their chemical stability in what is a very pernicious environment, i.e., chronic implantation in the body. The polyamide-acid coatings are then converted to polyimide coatings by one or more of the processes to be described.

One process comprises converting the polyamide-acids having recurring units of the following structural formula:

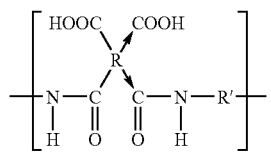

wherein → denotes isomerism, to polyimides by heating above 50° C. Heating serves to convert pairs of amide and carboxylic acid groups to imide groups. Heating may be conducted for a period of a few seconds to several hours. It has been found that after the polyamide-acid has been converted to the polyimide in accordance with the above describe heat conversion, if the polyimide is further heated to a temperature of 300°-500° C. for a short interval (15 seconds to 2 minutes), improvements in the thermal and hydrolytic stabilities of the polyimide are obtained as well as an increase in inherent viscosity.

A second process for converting the polyamide-acid composition to the polyimide thereof is a chemical treatment and involves treating the polyamide-acid composition with a dehydrating agent alone or in combination with a tertiary amine, e.g., acetic anhydride or an acetic anhydride-pyridine mixture. The ratio of acetic anhydride to pyridine may vary from just above zero to infinite mixtures. It is believed that the pyridine functions as a catalyst for the action of the cyclyzing agent, the acetic anhydride. Other possible dehydrating agents for use include propionic anhydride, butyric anhydride and similar fatty-acid anhydrides. Other tertiary amine catalysts include triethylamine, isoquinoline, a, b or gamma-picoline, 2,5-lutidine, etc A third process for conversion involves treatment with a carbodiimide, e.g., dicyclohexylcarbodiimide. The carbodiimide also serves to dehydrate the polyamide-acid and to act as an effective cyclyzing agent.

As a fourth process of conversion, a combination treatment may be used. The polyamide-acid may be partially converted to the polyimide in a chemical conversion treatment and then cyclization to the polyimide may be completed by subsequent heat treatment. The conversion of the polyamide-acid to the polyimide in the first step should not exceed 50% if it is desired to shape the composition into suitable forms. After shaping, the completion of the cyclization of the polyimide/polyamide-acid may be accomplished.

The presence of polyimides is evidenced by their insolubility in cold basic reagents as opposed to the rapid solubility of the polyamide-acid. Their presence is also apparent if the polyamide-acids are monitored by spectroscopy during conversion to the polyimide. The infrared spectra initially show a predominating absorption band at ca. 3.1 microns due to the NH bond. This band gradually disappears and as the reaction progresses, the polyimide absorption bands appear, a doublet at ca. 5.64 and 5.89 microns and a peak at 13.85 microns. When conversion is completed, the characteristic polyimide band predominates. In some cases, one can also detect minor amounts of isoimide linkages, i.e.

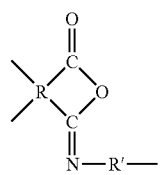

The starting materials for forming the products of the present invention are specific organic diamines and tetracarboxylic acid dianhydrides. The organic diamines are characterized by the formula $H_2NR'—NH_2$ wherein R' is a divalent benzenoid radical selected from the group consisting of

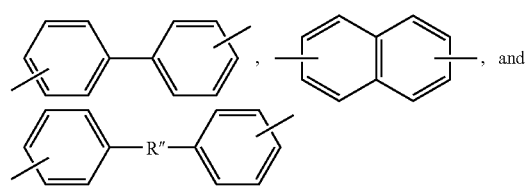

wherein R" is a divalent isoelectronic configuration comprising elements from Rows IVa, Va and VIa of the Periodic Table having an atomic weight of 12-33. Among the diamines which are suitable for use in the present invention are: 4,4'-diaminodiphenyl propane, 4,4'-diamino-diphenyl methane, benzidine, 3,3'-dichlorobenzidine, 4,4'-diamino-diphenyl sulfone, 4,4'-diamino-diphenyl ether, 1,5-diamino naphthaline, 4,4'-diamino-diphenyl diethylsilane, 4,4'-diamino-diphenyl diphenylsilane, 4,4'-diamino-diphenyl ethyl phosphine oxide, 4,4'-diamino-diphenyl phenyl phosphine oxide, 4,4'-diamino-diphenyl N-methyl amine, 4,4'-diamino-diphenyl N-phenyl amine and mixtures thereof.

The tetracarboxylic acid dianhydrides are characterized by the following formula:

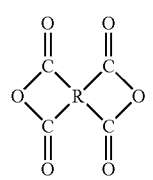

wherein R is a tetravalent organic radical containing at least 6 carbon atoms characterized by benzenoid unsaturation, wherein the 4 carbonyl groups of the dianhydride are each attached to separate carbon atoms and wherein each pair of carbonyl groups is directly attached to adjacent carbon atoms in the R group to provide a 5-membered ring as follows:

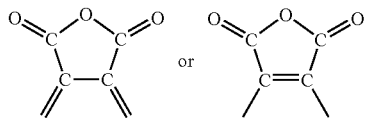

Illustrations of dianhydrides suitable for use in the present invention include: pyromellitic dianhydride, 2,3,6,7-naphthalene tetracarboxylic dianhydride, 3,3',4,4'-diphenyl tetracarboxylic dianhydride 1,2,5,6-naphthalene tetracarboxylic dianhydride, 2,2',3,3'-diphenyl tetracarboxylic dianhydride, 2,2-bits(3,4-dicarboxyphenyl) propane dianhydride, bis(3-4-diacarboxyphenyl) sulfone dianhydride, perylene 3,4,9,10-tetracarboxylic acid dianhydride, bis(3,4-dicarboxyphenyl) ether dianhydride, naphthlane-1,2,4,5-tetracarboxylic dianhydride, 2,2-bis(2,3-diacarboxyphenyl) propane dianhydride, 1,1-bis(2,3-dicarboxyphenyl) ethane dianhydride, 1,1-bis(3,4-dicarboxyphenyl) ethane dianhydride, bis(2,3-dicarboxyphenyl) methane dianhydride, bis(3,4-dicarboxyphenyl) methane dianhydride, benzene-1,2,3,4-tetracarboxylic dianhydride, pyrazine-2,3,5,6-tetracarboxylic dianhydride, thiophene-2,3,4,5-tetracarboxylic dianhydride, 3,4,3',4'-benzophenone tetracarboxylic dianhydride etc.

The solvents useful in the solution polymerization process for synthesizing the intermediate polyamide-acid compositions in the preferred process of preparing the polyimides are the organic solvents whose functional groups do not react with either of the reactants (the diamines or the dianhydrides) to any appreciable extent. Besides being inert to the system and, preferably, being a solvent for the product, the organic solvent must be a solvent for at least one of the reactants, preferably for both of the reactants. To state it another way, the organic solvent is an organic liquid other than either reactant or homologs of the reactants that is a solvent for at least 1 reactant, and contains functional groups, the functional groups being groups other than monofunctional primary and secondary amino groups and other than the monofunctional dicarboxylanhydro groups. The normally liquid organic solvents of the N,N-dialkylcarboxylamide class are useful as solvents in the process of this invention. The preferred solvents are the lower molecular weight members of this class that may easily be removed from the polyamide-acid and/or polyamide-acid shaped articles by evaporation, displacement or diffusion. Typical compounds of this useful class of solvents are: N,N-diethylformamide, N,N-diethylacetamide, N,N-dimethylmethoxy acetamide, N-methyl caprolactam, etc. Other solvents which may be useful in the present invention are: dimethylsulfoxide, N-methyl-2-pyrrolidone, tetramethylene urea, pyridine, dimethylsulfone, hexamethylphosphoramide, tetramethylene sulfone, formamide, N-methylformamide, butyrolactone and N-acetyl-2-pyrrolidone. The solvents can be used alone, in combinations of solvents, or in combination with poor solvents such as benzene, benzonitrile, dioxane, xylene, toluene and cyclohexane.

For convenience, abbreviations will be used whenever possible. Thus, DDP represents 4,4'-diamino-diphenyl propane; DDM, 4,4'-diamino-diphenyl methane; PP, benzidine; POP, 4,4'-diamino-diphenyl ether; PSP, 4,4'-diamino-diphenyl sulfide; $PSO_2P$, 4,4'-diamino-diphenyl sulfone; APDS, 4,4'-diamino-diphenyl diethylsilane; APPO, 4,4'-diamino-diphenyl phenyl-phosphine oxide; APMA, 4,4'-diamino-diphenyl N-methylamine; APP, 4,4'-diamino-diphenyl phenyl phosphonate; APDSO, 4,4'-diamino-diphenyl diethylsiloxane; PMDA, pyromellitic dianhydride; PPDA, 2,2-bis(3,4-dicarboxyphenyl) propane dianhydride; PEDA, bis(3,4-dicarboxyphenyl) ether dianhydride; $PSO_2DA$, bis(3,4-dicarboxyphenyl) sulfone dianhydride; DMF, N,N-dimethylformamide; DMA, N,N-diamthylacetamide; MP, N-methyl-2-pyrrolidone; T, toluene; P, pyridine; and AA, acetic anhydride.

Various coating chemistries within the scope of this invention are shown in Table I. The preparative conditions used are described above.

The pyromellitic dianhydride used was obtained as white crystals by sublimation of the commercial product through silica gel at 220-240° C. and 0.25-1 mm. mercury pressure.

N,N-diamethylformamide and N,N-dimethylacetamide were prepared by fractional distillation from phosphorous pentoxide; the fraction distilling at 47.5° C. and 17 mm. pressure being N,N-imethylformamide and the fraction distilling at 73° C. and 30 mm. pressure being N,N-dimethylacetamide.

More details of the coating chemistry are contained in U.S. Pat. No. 3,179,634, especially examples 1-35, at column 8, line 43 through column 16, line 45, all of which is incorporated by reference herein.

Further details of the chemistry and processes possibly of interest with respect to the present invention are included in the following:

| U.S. Patents | | |
|---|---|---|
| 3,179,614 | 3,287,311 | 5,478,916 |
| 3,179,630 | 3,990,098 | 5,502,157 |
| 3,179,631 | 4,056,651 | 5,639,850 |
| 3,179,632 | 5,171,828 | 5,741,883 |
| 3,179,633 | 5,464,928 | 6,048,959 |

U.S. PAP 2003/0216800 (Ebert et al.)
U.S. PAP 2005/0004643 (Ebert et al.)
S. J. Warner et al., 12 Solid State Nuclear Magnetic Resonance, 7185 (1998).

All of these references are incorporated by reference herein.

TABLE I

| Example | Gms. reactants Diamine | Dianhydride | Mls. solvent | Conversion |
|---|---|---|---|---|
| 1 | 20.0 DDM | 22.0 PMDA | 200 DMF | Heat. |
| 2 | 10.35 DDP | 10.0 PMDA | 60 DMF/P(1/1) | Do. |
| 3 | 3.0 DDM | 3.3 PMDA | 50 DMF | Do. |
| 4 | 9.15 POP | 10.0 PMDA | 100 DMF/P(3/2) | Do. |
| 5 | 9.38 PSP | 10.0 PMDA | 130 DMF/P(1/1/) | Do. |
| 6a | 5.17 DDP | 10.1 PMDA | 75 DMF/P(3/2) | Do. |
| 6b | 4.22 P | Same | Same | Same |
| 7[1] | 10.35 DDP | 10.0 PMDA | 50 DMF | Do. |
| 8[1] | 3.0 DDM | 3.3 PMDA | 50 DMF | Do. |
| 9 | 10.35 DDP | 10.0 PMDA | 56 DMF | (?). |
| 10 | 11.2 $PSO_2P$ | 10.0 PMDA | 75 DMF/P(2/1) | (?) |
| 11 | 2.01 PP | 2.37 PMDA | 50 DMA | P/AA. |
| 12a | 5.17 DDP | 10.1 PMDA | 75 DMF/P (3/2) | P/AA. |
| 12b | 4.22 PP | Same | Same | Same |
| 13 | 11.2 $PSO_2P$ | 10.0 PMDA | 150 DMF | P/AA. |
| 14 | 9.8 PSP | 10.0 PMDA | 180 DMF | P/AA. |
| 15 | 1.30 POP | 2.18 PPDA | 30P | Heat. |
| 16 | 80.0 POP | 87.1 PMDA | 464 DMA | Do. |
| 17 | 12.0 POP | 13.0 PMDA | 191 DMA | Do. |
| 18 | 0.7 POP | 1.00 PEDA | 25 DMA | Do. |
| 19 | 4.0 POP | 4.34 PMDA | 75 DMA | Do. |
| 20 | 27.5 APDS | 22 PMDA | 200 DMF | Do. |
| 21 | 31.4 APPO | 22 PMDA | 200 DMF | Do. |
| 22 | 21.6 APMA | 22 PMDA | 200 DMF | Do. |
| 23 | 7.6 PSP | 12.5 $PSO_2DA$ | 200 DMF | Do. |
| 24 | 3.0 DDM | 3.3 PMDA | 50 DMF | Do. |
| 25-31 | POP | PMDA | DMA | P/AA. |
| 32-33 | POP | PMDA | DMA/MP/T | Heat. |

TABLE I-continued

| Example | Gms. reactants Diamine | Dianhydride | Mls. solvent | Conversion |
|---|---|---|---|---|
| 34 | APP | PMDA | DMF | Do. |
| 35 | APDSO | PMDA | DMF | Do. |

[1] In Examples 7-8, 50 mole percent of the acid groups in the polyamid-acid solution were converted to the triethylammonium salt.
[2] In Examples 9-10, stoichlometric amounts of acetic anhydride/pyridine were added to polyamide-acid solutions to convert 30 mole percent of the polyamide-acid groups to the corresponding polyimide prior to final conversion by heating.

While a particular embodiment of the present invention has been shown and described, modifications may be made. It is therefore intended in the appended claims to cover all such changes and modifications, which fall within the true spirit and scope of the invention.

What is claimed is:

1. An implantable medical device, comprising:
   a lead body extending from a proximal end to a distal end;
   a plurality of conductors extending between the proximal end and the distal end of the lead body; and
   a single insulative layer positioned about each of the plurality of conductors, wherein the insulative layer is formed of an aromatic polyimide of the following structure:

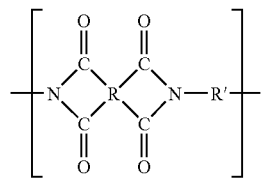

(I)

wherein R is a tetravalent aromatic radical, preferably containing at least one ring of six carbon atoms, said ring characterized by benzenoid unsaturation, the four carbonyl groups being attached directly to separate carbon atoms in a ring and each pair of carbonyl groups being attached to adjacent carbon atoms in a ring of the R radical; and wherein R" is a divalent benzenoid radical selected from the group consisting of

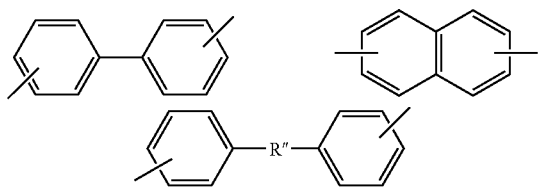

wherein R" is selected from the group consisting of an alkylene chain having 1-3 carbon atoms,

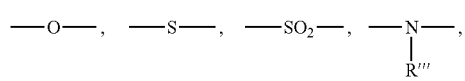

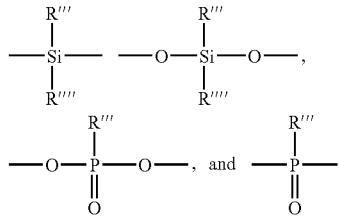

-continued wherein R''' and R'''' are selected from the group consisting of alkyl and aryl.

2. The implantable medical device of claim 1, wherein the insulative layer has a thickness of between approximately 0.0001 inches and approximately 0.0050 inches.

3. The implantable medical device of claim 1, wherein the insulative layer is positioned about the plurality of conductors in multiple coats to form multiple layers.

4. The implantable medical device of claim 1, wherein the plurality of conductors form a conductor coil having an outer diameter between approximately 0.010 inches and approximately 0.110 inches.

5. The implantable medical device of claim 1, wherein one or more of the plurality of conductors form a single circuit.

6. The implantable medical device of claim 1, further comprising a redundant insulative layer positioned about the plurality of conductors.

7. The implantable medical device of claim 6, wherein the redundant insulative layer is formed of a material having a flex modulus less than the insulative layer surrounding the plurality of conductors.

8. An implantable medical device, comprising:
   a housing generating electrical signals for delivering therapy, the housing having a connector block;
   a lead having a lead body extending from a proximal end to a distal end, the proximal end of the lead body being insertable within the connector block and electrically coupling the housing and the lead;
   a plurality of conductors extending between the proximal end and the distal end of the lead body;
   and an insulative layer positioned about the plurality of conductors, wherein the insulative layer is formed of a aromatic polyimide having the following structure:

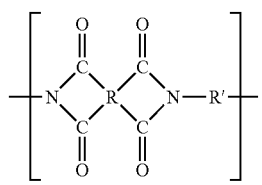

(I)

wherein R is a tetravalent aromatic radical, preferably containing at least one ring of six carbon atoms, said ring characterized by benzenoid unsaturation, the four carbonyl groups being attached directly to separate carbon atoms in a ring and each pair of carbonyl groups being attached to adjacent carbon atoms in a ring of the R radical; and wherein R' is a divalent benzenoid radical selected from the group consisting of

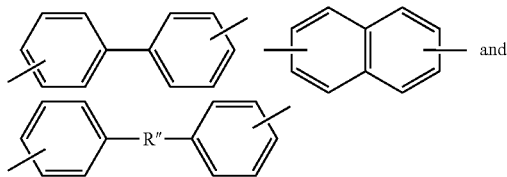

wherein R'' is selected from the group consisting of an alkylene chain having 1-3 carbon atoms,

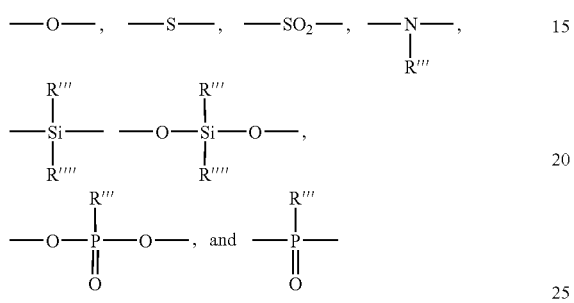

wherein R''' and R'''' are selected from the group consisting of alkyl and aryl.

9. The implantable medical device of claim 8, wherein the insulative layer has a thickness of between approximately 0.0001 inches and approximately 0.0050 inches.

10. The implantable medical device of claim 8, wherein the insulative layer is positioned about the plurality of conductors in multiple coats to form multiple layers.

11. The implantable medical device of claim 8, wherein the plurality of conductors form a conductor coil having an outer diameter between approximately 0.010 inches and approximately 0.1 10 inches.

12. The implantable medical device of claim 8, wherein one or more of the plurality of conductors forms a single circuit.

13. The implantable medical device of claim 8, further comprising a redundant insulative layer positioned about the plurality of conductors.

14. A guidewire comprising proximal, medial, and distal segments, the guidewire having coated on some portion of at least one of the segments an aromatic polyimide having the structure:

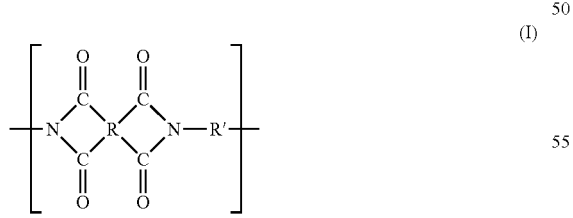

wherein R is a tetravalent aromatic radical, preferably containing at least one ring of six carbon atoms, said ring characterized by beuzenoid unsaturation, the four carbonyl groups being attached directly to separate carbon atoms in a ring and each pair of carbonyl groups being attached to adjacent carbon atoms in a ring of the R radical; and wherein R' is a divalent benzenoid radical selected from the group consisting of

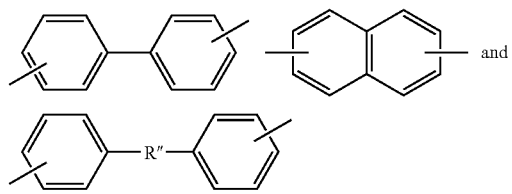

wherein R'' is selected from the group consisting of an alkylene chain having 1-3 carbon atoms,

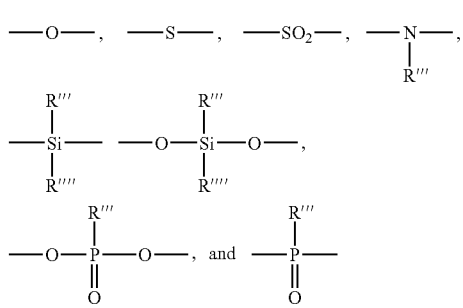

wherein R''' and R'''' are selected from the group consisting of alkyl and aryl.

15. A method for manufacturing a medical device, the method comprising the step of forming on at least some portion of the device a layer of aromatic polyimide of the structure:

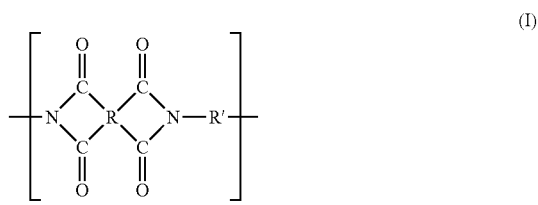

wherein R is a tetravalent aromatic radical, preferably containing at least one ring of six carbon atoms, said ring characterized by benzenoid unsaturation, the four carbonyl groups being attached directly to separate carbon atoms in a ring and each pair of carbonyl groups being attached to adjacent carbon atoms in a ring of the R radical; and wherein R' is a divalent benzenoid radical selected from the group consisting of

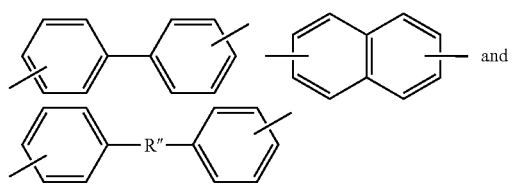

wherein R'' is selected from the group consisting of an alkylene chain having 1-3 carbon atoms,

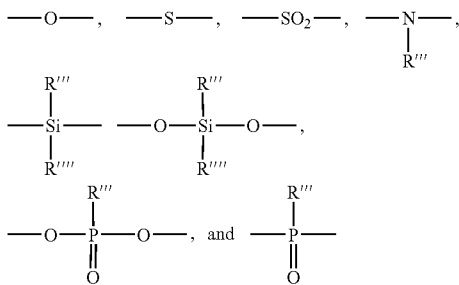

wherein R''' and R'''' are selected from the group consisting of alkyl and aryl.

16. The method of claim 15, wherein the forming step comprises a dip coating process.

17. The method of claim 15, wherein the forming step comprises a spray coating process.

18. The method of claim 15, wherein the forming step comprises an extrusion process.

19. The method of claim 15, further comprising the step of forming an additional layer of aromatic polyimide on the lead conductor.

20. The method of claim 15, further comprising the step of forming multiple additional layers of aromatic polyimide on the device.

21. The method of claim 15, further comprising the step of forming an insulative layer of material over the layer of aromatic polyimide.

22. The method of claim 21, wherein the insulative layer comprises a fluoropolymer.

23. A method according to claim 15 wherein the device is a medical electrical lead comprising at least one elongate lead conductor.

24. The method of claim 23, further comprising the step of winding the lead conductor into a coil.

25. The method of claim 24, wherein the step of winding precedes the step of forming.

26. The method of claim 24, wherein the step of winding follows the step of forming.

27. The method of claim 24, further comprising the step of bundling the conductor with a plurality of other lead conductors to form a cable.

28. A medical electrical lead, comprising a conductor including a single insulative layer of aromatic polyimide, the aromatic polyimide having the structure:

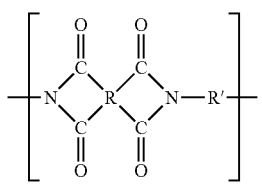

(I)

wherein R is a tetravalent aromatic radical, preferably containing at least one ring of six carbon atoms, said ring characterized by benzenoid unsaturation, the four carbonyl groups being attached directly to separate carbon atoms in a ring and each pair of carbonyl groups being attached to adjacent carbon atoms in a ring of the R radical; and wherein R' is a divalent benzenoid radical selected from the group consisting of

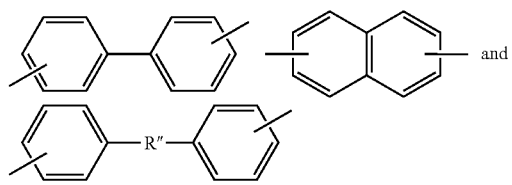

wherein R'' is selected from the group consisting of an alkylene chain having 1-3 carbon atoms,

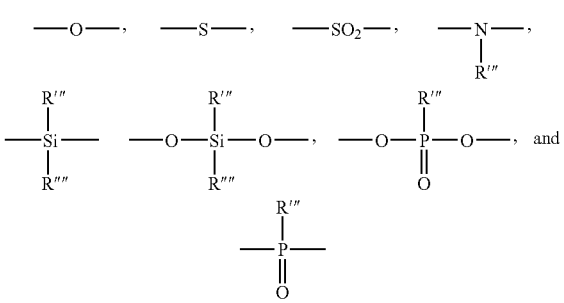

wherein R''' and R'''' are selected from the group consisting of alkyl and aryl.

29. The lead of claim 28, wherein the conductor further includes another layer of aromatic polyimide formed thereover.

30. The lead of claim 28, wherein the conductor further includes multiple additional layers of aromatic polyimide formed thereover.

31. The lead of claim 28, wherein the conductor further includes a plurality of bundled wire strands extending within the layer of aromatic polyimide.

32. The lead of claim 28, wherein the conductor is a one of a plurality of bundled wire strands.

33. The lead of claim 28, wherein the conductor is a one of a plurality of coiled wire filars.

34. The lead of claim 28, wherein the conductor further includes a layer of fluoropolymer formed over the layer of aromatic polyimide.

35. A medical device including on at least some portion thereof a polyimide of the structure:

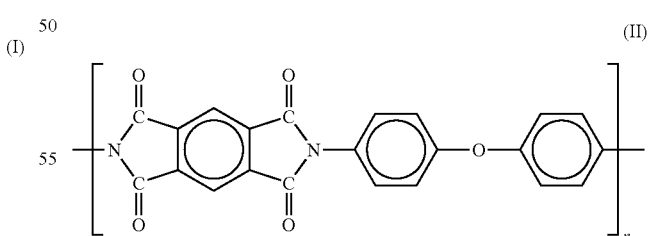

(II)

wherein "n" has a value in the range of about 50 to 500.

36. An aromatic polyimide according to claim 35 wherein "n" has a value in the range of 75 to 400.

37. An aromatic polyimide according to claim 35 wherein "n" has a value in the range of 100 to about 350.

* * * * *